United States Patent [19]

Bernhard et al.

[11] Patent Number: 4,519,825
[45] Date of Patent: May 28, 1985

[54] PROCESS FOR RECOVERING $C_4+$ HYDROCARBONS USING A DEPHLEGMATOR

[75] Inventors: Dennis P. Bernhard, Allentown; Howard C. Rowles, Center Valley; Robert L. Teichman, Allentown, all of Pa.

[73] Assignee: Air Products and Chemicals, Inc., Allentown, Pa.

[21] Appl. No.: 488,328

[22] Filed: Apr. 25, 1983

[51] Int. Cl.³ .................................................. F25J 3/02
[52] U.S. Cl. .......................................... 62/28; 62/31; 62/34; 62/39
[58] Field of Search ......................... 62/9, 11, 24–28, 62/38, 39, 31, 34

[56] References Cited

U.S. PATENT DOCUMENTS

| | | |
|---|---|---|
| 3,274,102 | 9/1966 | Brazell et al. . |
| 4,002,042 | 1/1977 | Pryor et al. . |
| 4,140,504 | 2/1979 | Campbell et al. . |
| 4,270,940 | 6/1981 | Rowles et al. . |

Primary Examiner—Frank Sever
Attorney, Agent, or Firm—Mark L. Rodgers; James C. Simmons; E. Eugene Innis

[57] ABSTRACT

A process is described for separating $C_4+$ hydrocarbons in high recovery and high purity from a feed gas comprising about 0–5% $C_5$ and heavier hydrocarbons, 1–10% $C_4$ hydrocarbons, 0–10% $C_3$ hydrocarbons, 0–10% $C_2$ hydrocarbons and the balance $CH_4$ and light inerts. Efficient separation is effected by using a dephlegmator cycle employing only internal refrigeration.

8 Claims, 2 Drawing Figures

PROCESS FOR RECOVERING $C_4+$ HYDROCARBONS USING A DEPHLEGMATOR

TECHNICAL FIELD OF THE INVENTION

This invention relates to the recovery of $C_4$ and heavier hydrocarbons from a gas stream containing $C_4+$ hydrocarbons and light volatile components.

BACKGROUND OF THE INVENTION

There are several major processes known in the art for recovering hydrocarbons from dehydrogenation processes or lean refinery-type gas mixtures. One such method is oil scrubbing, wherein heavy hydrocarbons are absorbed from the feed gas by a circulating heavy oil in an absorber column and are then recovered in a stripping column. The non-condensable vapor overhead from the stripping column may be recycled back through the absorber column for enhanced recovery. An example of this type of process is described in U.S. Pat. No. 3,274,102.

A second method for recovering hydrocarbons from a natural gas or similar refinery or process stream is by cryogenic partial condensation. As described in U.S. Pat. No. 4,140,504, the gas is cooled at high pressure to produce vapor and liquid portions. The liquid portion from the partial condensation is further cooled and then expanded to a lower pressure. At the lower pressure, the liquid is supplied to a distillation column, where it is separated into fractions. The vapor portion is work-expanded to the operating pressure of the distillation column and supplied to the distillation column below the feed point of the expanded liquid portion. The liquid product is then revaporized to provide refrigeration for the system. The low pressure product gas is compressed and reliquified before it is recovered.

Two processes for recovering hydrocarbons from a feed gas using dephlegmator cycles are disclosed in U.S. Pat. Nos. 4,002,042 and 4,270,940. In U.S. Pat. No. 4,002,042 a feed gas containing $C_2+$ hydrocarbons and lighter components is introduced to a dephlegmator to effect its separation into a vapor stream and a condensate stream. An extraneous refrigerant, such as ethylene, is evaporated in the dephlegmator to provide refrigeration for the system. The condensation stream is then passed to a demethanizer column where it is fractionated into an overhead methane-hydrogen stream and a bottom product ethylene-ethane stream. In this process a large fraction of the $C_2+$ is initially recovered upstream of the dephlegmator in a heat exchanger, or in a series of heat exchangers, as in a typical ethylene plant.

U.S. Pat. No. 4,270,940 discloses a dephlegmator cycle for recovering $C_2$ hydrocarbons. In this process enhanced recovery of ethane and ethylene from demethanizer column overhead is obtained by subjecting the uncondensed vapor effluent from the main reflux condenser to further condensation and accompanying rectification in a dephlegmator and returning the liquid condensate from the dephlegmator to the demethanizer column. A large portion, e.g., 95% or more, of the $C_2$ hydrocarbons are separated initially in the demethanizer column before the uncondensed vapor from the main reflux condenser enters the dephlegmator. The $C_2+$ hydrocarbons which remain in the main condenser effluent vapor stream are condensed in the dephlegmator and the liquid condensate is then recycled back through the demethanizer to obtain the final high $C_2$ recovery. The liquid condensate recovered from the dephlegmator is of low purity, e.g. 5 to 10 mole % $C_2+$, and must be fractionated in the demethanizer to remove the 85% or more $CH_4$ impurity.

BRIEF SUMMARY OF THE INVENTION

We have found a particular dephlegmator cycle which provides a simple and efficient method for recovering $C_4+$ hydrocarbons in high yield and high purity from a feed gas comprising about 0 to 5 mole % $C_5$ and heavier hydrocarbons, 1-10% $C_4$ hydrocarbons, 0-10% $C_3$ hydrocarbons, 0-10% $C_2$ hydrocarbons, and the balance $CH_4$ and light inerts. The process for this $C_4+$ recovery comprises pressurizing the feedstream to a level of from 10 to 40 atmospheres, if it is not at that level, and establishing a feedstream temperature of from about 2° to 38° C. The feedstream is then passed through a dephlegmator where it is cooled to a preselected overhead temperature, from about $-52°$ to $-76°$ C., for forming a liquid condensate containing $C_4+$ hydrocarbons and an overhead vapor fraction. The $C_4+$ liquid condensate is then withdrawn from the dephlegmator in high purity. Refrigeration for effective cooling in said dephlegmator is established and maintained by withdrawing an overhead vapor fraction from the dephlegmator and warming by indirect heat exchange against the feed in the dephlegmator. The warmed overhead vapor fraction is work expanded in an expander to a pressure sufficient to generate a cold fraction having a temperature from about 2° to 12° C. below the preselected overhead temperature in said dephlegmator. The cold fraction is then withdrawn from the expander and again warmed by indirect heat exchange against the feed in the dephlegmator.

As can be seen from the art, a number of separation techniques have been developed to recover hydrocarbons from a feed gas. The present invention, however, allows for high recovery of $C_4+$ hydrocarbons from a defined feed stream without the expensive equipment necessary for an oil scrubbing or partial condensation process, and without the necessity of employing external refrigeration or an initial fractionating step as with the previously described dephlegmator processes.

DETAILED DESCRIPTION OF THE INVENTION

Figure 1:
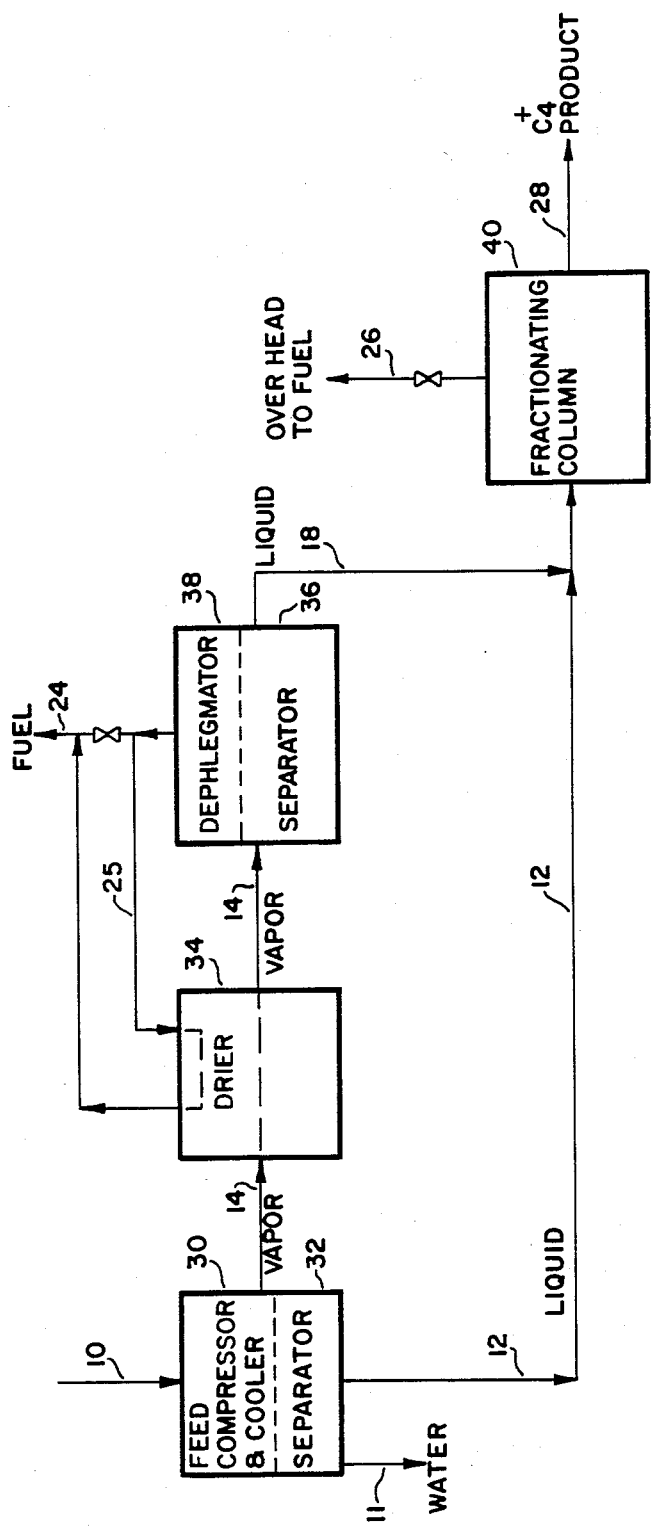
FIG. 1 is a schematic flow diagram of a separation and recovery system according to one embodiment of the invention.

As shown in FIG. 1, a feed stream 10 comprising about 0-5 mole % $C_5$ and heavier hydrocarbons, 1-10% $C_4$ hydrocarbons, 0-10% $C_3$ hydrocarbons, 0-10% $C_2$ hydrocarbons, and the balance $CH_4$ and light inerts, e.g. $H_2$, $CO$, $N_2$, and $CO_2$, enters a treatment zone 30. The $C_4$ and heavier hydrocarbons can be any type of hydrocarbon or combination of hydrocarbons including alkanes, iso-paraffins, olefins, diolefins, cycloparaffins, and aromatics. In said treatment zone 30, the feed stream 10 is compressed to a level of 10 to 40 atmospheres, if not already at that level, and cooled to a temperature of between about 2° to 38° C., which may result in partial condensing of a portion of said feed stream. The feed temperature should preferably not be more than 20° C. above the hydrocarbon dewpoint of the feed in order to achieve efficient recovery of refrigeration in the dephlegmator. Treatment zone 30 can comprise any conventional compression and cooling means known in the art. The source of the feed gas is not important, however, the present invention is especially adaptable to dehydrogenation process or refinery-type streams. When applied to a particular feed stream as defined above, the present process provides for greater $C_{4+}$ hydrocarbon recovery at a given power output than the prior art processes. If high levels of $C_4$ and heavier hydrocarbons, e.g., more than 15%, are present in the feed, however, or an excess of $C_2$–$C_3$ hydrocarbons, e.g., more than 20%, the present process is not economically feasible. Similarly, the process is not economical if low recovery, e.g., less than 50%, of the $C_{4+}$ hydrocarbons, is acceptable.

The treated feed stream is then passed through a separator 32 where any condensed liquid is separated from the gaseous vapor. The condensed liquid stream 12 can be sent directly to a fractionating column 40, such as a depropanizer column, where $C_{4+}$ hydrocarbons are recovered and residual light components are rejected, or a debutanizer column, where $C_4$ and $C_{5+}$ hydrocarbons are separated. If the condensed liquid consists essentially of water, it can be removed from separator 32, via line 11.

The vapor stream 14 can optionally be passed through a drier 34 where excess moisture can be removed to prevent frost build-up in the system. Such a drier is only necessary if the feed leaving the separator 32 is not sufficiently dry, and therefore is only one embodiment of the present invention and not a necessary part thereof. If such a drier is employed it can be any type drying means commonly known in the art.

Figure 2:
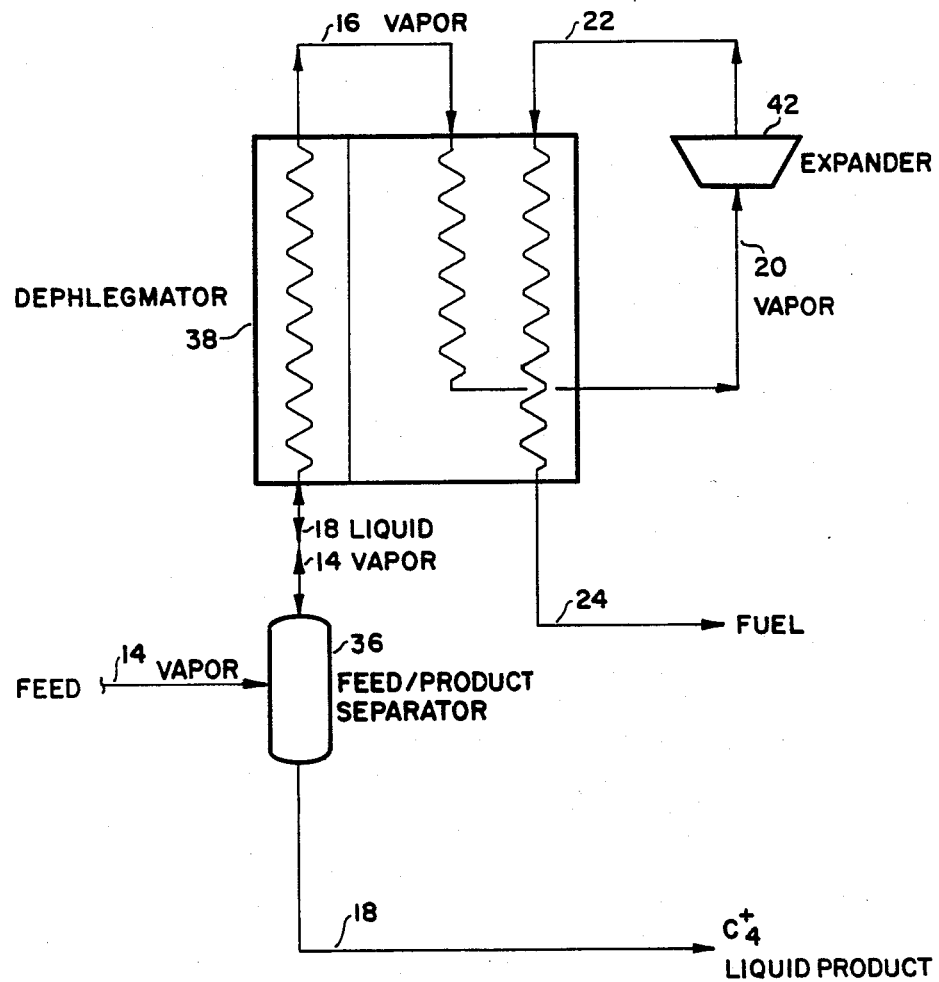
FIG. 2 is a process flow diagram for the dephlegmator and refrigeration cycle.

The vapor stream 14, either from a drier 34 or directly from the separator 32, is sent to a feed/product separator 36 where the vapor feed stream is then directed to a dephlegmator 38. In the dephlegmator 38, the vapor stream is cooled to a preselected overhead temperature, within the range from −52° to −76° C., for forming a high purity $C_{4+}$ liquid condensate 18 and an overhead vapor fraction containing undesirable lighter components. The refrigeration value of the vapor fraction comprising lighter components is recovered as shown in FIG. 2 and then rejected from the dephlegmator as a fuel product 24. A portion of the fuel stream 34 may be used to regenerate a dessicant-type drier, as shown by stream 25. The $C_{4+}$ liquid condensate 18 is passed through the feed product separator and recovered in a high yield, i.e. about 95% recovery, and high purity, i.e. at least 60 mole % and preferably at least 75%, $C_{4+}$ product. Preferably, but not necessarily, the high purity $C_{4+}$ liquid condensate 18 is sent to a fractionating column 40, such as a depropanizer, where residual $C_3$ and lighter hydrocarbons are rejected as a fuel stream 26 and a further purified $C_{4+}$ stream 28 results.

FIG. 2 of the drawings illustrates the process flow in the dephlegmator 38. Feed streams and apparatus which are common to both FIG. 1 and FIG. 2 are numbered the same. The feed stream 14 pressurized to 10 to 40 atmospheres, passes through the feed/product separator 36 and enters the dephlegmator 38. As the feed flows up through the dephlegmator 38, it is cooled to a preselected overhead temperature, from about −52° to −76° C. Essentially all, i.e., at least 95% and preferably at least 98% of the $C_{4+}$ hydrocarbons are condensed at this preselected temperature, and the condensed fluid stream 18 flows downward as the feed 14 flows upward in the dephlegmator 38. The rectified liquid stream 18 exits the dephlegmator 38 and is collected in the feed/product separator 36. The rectified liquid product stream 18 can then be recovered from the feed/product separator 36 and, if desired, it can be passed through a fractionator, such as a depropanizer column, to further purify the $C_{4+}$ product stream, or through a debutanizer to separate the $C_4$ and $C_{5+}$ hydrocarbons.

Refrigeration for this process is provided by withdrawing the overhead vapor stream 16 from said dephlegmator 38 and warming by indirect heat exchange against the feed stream 14 entering the dephlegmator 38. This resulting warm vapor stream 20 is then work expanded in an expander 42 to a pressure sufficient to generate a cold fraction 22 having a temperature from about 2° to 15° C. below the preselected overhead temperature in the dephlegmator 38. For example, if the preselected overhead temperature in the dephlegmator is −60° C., the warm vapor stream would be expanded to effect a temperature from about −62° to −75° C. at a pressure sufficient to provide the required refrigeration. The resulting cold stream 22 is then withdrawn from the expander 42 and warmed again by indirect heat exchange against the feed stream 14 entering the dephlegmator, thereby cooling said incoming feed stream 14. This warmed fraction 24 is then withdrawn from the dephlegmator and used as fuel or for some other purpose.

In the dephlegmator, under specific conditions, the $C_{4+}$ hydrocarbons are condensed as the feed is cooled. The condensed liquid flows downward as the vapor flows upward resulting in rectification of the $C_{4+}$ product to a high purity with high recovery. The $C_{4+}$ product is recovered as an all-liquid stream at the feed gas pressure. No external refrigeration or other energy input is necessary for this process, provided all the operating conditions are met, as all required refrigeration is provided by reheating the vapor exiting the top of the dephlegmator and work expanding the gas through a turbine or other type expander.

EXAMPLE 1

The present process was used to treat the gas stream generated from a dehydrogenation process containing about 7.4 mole % $C_{4+}$ hydrocarbons. The material balance for this process is reported in Table 1 below. The stream numbers refer to the points as represented in FIG. 2.

TABLE 1

| Stream Number | 14 | 16 | 18 | 20 | 22 | 24 |
|---|---|---|---|---|---|---|
| Pressure (atm) | 28.7 | 28.7 | 28.7 | 28.5 | 7.0 | 6.7 |
| Temperature (°C.) | 18.8 | −57.8 | 9.7 | 4.4 | −60.0 | 16.9 |
| Flow Rates (Moles/hr.) | | | | | | |
| Hydrogen | 1,675.08 | 1,671.04 | 4.04 | 1,671.04 | 1,671.04 | 1,671.04 |
| Carbon Monoxide | 4.77 | 4.75 | 0.02 | 4.75 | 4.75 | 4.75 |
| Nitrogen | 343.83 | 341.77 | 2.06 | 341.77 | 341.77 | 341.77 |
| Carbon Dioxide | 36.77 | 35.32 | 1.45 | 35.32 | 35.32 | 35.32 |

TABLE 1-continued

| Stream Number | 14 | 16 | 18 | 20 | 22 | 24 |
|---|---|---|---|---|---|---|
| Methane | 117.95 | 116.12 | 1.83 | 116.12 | 116.12 | 116.12 |
| Ethylene | 6.60 | 6.20 | 0.40 | 6.20 | 6.20 | 6.20 |
| Ethane | 5.47 | 4.98 | 0.49 | 4.98 | 4.98 | 4.98 |
| Propylene | 34.21 | 24.54 | 9.67 | 24.54 | 24.54 | 24.54 |
| Propane | 16.46 | 10.79 | 5.67 | 10.79 | 10.79 | 10.79 |
| Butanes | 179.13 | 2.69 | 176.44 | 2.69 | 2.69 | 2.69 |
| Pentane | 0.27 | 0.00 | 0.27 | 0.00 | 0.00 | 0.00 |
| Total Flow (Mole/hr.) | 2,420.54 | 2,218.20 | 202.34 | 2,218.20 | 2,218.20 | 2,218.20 |
| Mole % | | | | | | |
| Hydrogen | 69.21 | 75.34 | 2.00 | | | |
| Carbon Monoxide | 0.20 | 0.21 | 0.01 | | | |
| Nitrogen | 14.20 | 15.41 | 1.02 | | | |
| Carbon Dioxide | 1.52 | 1.59 | 0.72 | | | |
| Methane | 4.87 | 5.23 | 0.90 | | | |
| Ethylene | 0.27 | 0.28 | 0.20 | | | |
| Ethane | 0.23 | 0.22 | 0.24 | | | |
| Propylene | 1.41 | 1.11 | 4.78 | | | |
| Propane | 0.68 | 0.49 | 2.80 | | | |
| Butanes | 7.40 | 0.12 | 87.20 | | | |
| Pentane | 0.01 | 0.00 | 0.13 | | | |

A comparison of the flow rate of $C_4+$ hydrocarbons entering the system, stream 14, with the flow rate in the liquid product exiting the dephlegmator, stream 18, shows that the dephlegmator cycle recovers about 98.5% of the $C_4+$ hydrocarbons in the feedstream as a liquid product at the feed gas pressure. The composition of stream 18 indicates that the liquid leaving the dephlegmator contains 87.3 mole % $C_4+$ hydrocarbons.

In order to effect the same percent recovery using partial condensation, product $C_4+$ purity is only about 72.5 mole %. Since more unwanted light components are contained in the $C_4+$ product stream, more refrigeration for condensation is required than with a dephlegmator cycle. Therefore, ¼ to ⅓ of the $C_4+$ product must be revaporized at about 4 atmospheres to provide additional refrigeration above that provided by the expander. This $C_4+$ vapor product portion must then be compressed and reliquified for any further processing. Alternatively, an equivalent amount of external refrigeration must be supplied at temperatures as low as $-60°$ C.

As compared to the oil-scrub process, equipment and energy savings are also realized by using a dephlegmator cycle. This is due to the fact that with the oil-scrub process the $C_4+$ product is recovered as a low pressure, low purity vapor from the overhead of the stripping column. This vapor must then be liquified for further processing and purification. Non-condensable vapor must be compressed and recycled to the absorber to achieve high $C_4+$ recovery. A large heat energy input to the stripping column is also required.

Since the dephlegmator cycle yields a higher purity $C_4+$ product than the prior art processes, the feed $C_4+$ exiting the system contains less light components which enter any downstream equipment for further purification, such as a depropanizer or $C_4/C_5$ separation column. This provides further energy savings in the downstream purification process. The present invention is also superior to the prior art dephlegmation processes in that all the refrigeration is internal and the system provides for direct recovery of high purity liquid $C_4+$ product without the necessity of first fractionating the feed stream in a demethanizer or similar type column.

EXAMPLE 2

The present process was also applied to a leaner refinery gas feed containing 1.8 mole % $C_4+$ hydrocarbons. The material balance for this process is reported in Table 2 below. The stream numbers refer to the points as represented in FIG. 2.

TABLE 2

| Steam Number | 14 | 16 | 18 | 20 | 22 | 24 |
|---|---|---|---|---|---|---|
| Pressure (atm) | 15.3 | 15.3 | 15.3 | 15.2 | 5.3 | 5.0 |
| Temperature (°C.) | 26.6 | −64.0 | −11.6 | −28.9 | −73.2 | 1.4 |
| Flow Rates (Moles/hr.) | | | | | | |
| Hydrogen | 2,200.00 | 2,199.44 | 0.56 | 2,199.44 | 2,199.44 | 2,199.44 |
| Methane | 105.00 | 104.80 | 0.20 | 104.80 | 104.80 | 104.80 |
| Ethane | 105.00 | 102.73 | 2.27 | 102.73 | 102.73 | 102.73 |
| Propane | 60.00 | 49.54 | 10.46 | 49.54 | 49.54 | 49.54 |
| Butanes | 26.20 | 0.64 | 25.56 | 0.64 | 0.64 | 0.64 |
| Isopentane | 4.00 | 0.00 | 4.00 | 0.00 | 0.00 | 0.00 |
| Pentane | 3.00 | 0.00 | 3.00 | 0.00 | 0.00 | 0.00 |
| Hexane | 6.30 | 0.00 | 6.30 | 0.00 | 0.00 | 0.00 |
| Benzene | 3.00 | 0.00 | 3.00 | 0.00 | 0.00 | 0.00 |
| Toluene | 2.00 | 0.00 | 2.00 | 0.00 | 0.00 | 0.00 |
| Total Flow Mole/hr. | 2,514.50 | 2,457.15 | 57.35 | | | |
| Mole % | | | | | | |
| Hydrogen | | 87.48 | 89.51 | 0.98 | | |
| Methane | | 4.18 | 4.26 | 0.35 | | |
| Ethane | | 4.18 | 4.18 | 3.96 | | |
| Propane | | 2.39 | 2.02 | 18.23 | | |
| Butanes | | 1.04 | 0.03 | 44.57 | | |
| Isopentane | | 0.16 | 0.00 | 6.97 | | |
| Pentane | | 0.12 | 0.00 | 5.23 | | |
| Hexane | | 0.25 | 0.00 | 10.99 | | |
| Benzene | | 0.12 | 0.00 | 5.23 | | |
| Toluene | | 0.08 | 0.00 | 3.49 | | |

A comparison of the flow rates of $C_4+$ hydrocarbons entering the system, stream 14, with the flow rates leaving the dephlegmator, stream 18, indicates that the dephlegmator process recovers about 98.5% of the $C_4+$ hydrocarbons as a liquid product. The composition of stream 18 leaving the dehlegmator shows a $C_4+$ purity of about 76.5 mole %.

In order to effect the same percent recovery using a partial condensation cycle, product $C_4+$ purity is only about 31.5 mole % due to the lean composition of the feed. Also, about one-half of the product must be revaporized at about 5.3 atmospheres for further refrigeration in addition to the expander.

The same advantages over the oil-scrub process and prior art dephlegmator processes which were described in Example 1 for treating a gas stream generated by a dehydrogenation process are also realized using this leaner refinery-type gas feed.

Having thus described the present invention, what is now deemed appropriate for Letters Patent is set out in the following appended claims.

What is claimed:

1. A process for separating $C_4$ and heavier hydrocarbons in high recovery and a purity of at least 60 mole %, from a feed gas comprising about 0–5 mole % $C_5$ and heavier hydrocarbons, 1–10% $C_4$ hydrocarbons, 0–10% $C_3$ hydrocarbons, 0–10% $C_2$ hydrocarbons, and the balance $CH_4$ and light inerts, which comprises:
    (a) pressurizing the feed gas to a level from 10 to 40 atmospheres if not at said level;
    (b) establishing and maintaining said feed gas at a temperature of from 2° to 38° C.;
    (c) passing said feed gas, prior to fractionation, to a dephlegmator, thereby cooling said feed gas to a preselected overhead temperature, within the range from −52° to −76° C., for forming a liquid condensate containing $C_4+$ hydrocarbons of a purity of at least 60 mole % and an overhead vapor fraction;
    (d) withdrawing said liquid condensate from the dephlegmator;
    (e) withdrawing said overhead vapor fraction from said dephlegmator and warming by indirect heat exchange against the feed in said dephlegmator;
    (f) work expanding the resulting warmed overhead vapor fraction in an expander to a pressure sufficient to generate a cold fraction having the required refrigeration value and having a temperature from about 2° to 15° C. below the preselected overhead temperature in said dephlegmator; and
    (g) withdrawing said cold fraction from the expander and again warming by indirect heat exchange against the feed in said dephlegmator.

2. A process in accordance with claim 1 wherein the feed gas is dried prior to entering the dephlegamator.

3. A process in accordance with claim 1 wherein the liquid condensate withdrawn from the dephlegmator is subsequently passed through a depropanizer column.

4. A process in accordance with claim 1 wherein the feed gas is a refinery-type stream, or a stream generated by a dehydrogenation process.

5. A process in accordance with claim 1 wherein said $C_4$ and heavier hydrocarbons are selected from the group consisting of iso-paraffins, olefins, diolefins, cycloparaffins, aromatics, or any combination thereof.

6. A process in accordance with claim 1 wherein recovery of at least 95% of said $C_4$ and heavier hydrocarbons, and preferably at least 98%, is achieved.

7. A process in accordance with claim 1 wherein the purity of the combined $C_4$ and heavier hydrocarbon liquid condensate withdrawn from said dephlegmator is at least 75 mole %.

8. A process in accordance with claim 1 wherein said established temperature of said feed stream is less than or equal to 20° C. above the hydrocarbon dewpoint of said feed stream.

* * * * *

UNITED STATES PATENT AND TRADEMARK OFFICE
CERTIFICATE OF CORRECTION

PATENT NO. : 4,519,825

DATED : 28 May 1985

INVENTOR(S) : Dennis P. Bernhard, Howard C. Rowles, Robert L. Teichman

It is certified that error appears in the above-identified patent and that said Letters Patent is hereby corrected as shown below:

Column 3, Line 46
    Delete stream "34" and substitute therefor stream -- 24 --

Signed and Sealed this

Tenth Day of December 1985

[SEAL]

Attest:

DONALD J. QUIGG

Attesting Officer      Commissioner of Patents and Trademarks